United States Patent
Lin et al.

(10) Patent No.: US 12,139,515 B2
(45) Date of Patent: Nov. 12, 2024

(54) DEXTRAN AFFINITY TAG AND USE THEREOF

(71) Applicant: AGRICULTURAL TECHNOLOGY RESEARCH INSTITUTE, HsinChu (TW)

(72) Inventors: Jiunn-Horng Lin, HsinChu (TW); Jyh-Perng Wang, HsinChu (TW); Zeng-Weng Chen, HsinChu (TW); Wen-Zheng Huang, HsinChu (TW); You-Lin Zhuo, HsinChu (TW); Shih-Ling Hsuan, HsinChu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 729 days.

(21) Appl. No.: 17/289,475

(22) PCT Filed: Oct. 29, 2018

(86) PCT No.: PCT/CN2018/112303
§ 371 (c)(1),
(2) Date: Apr. 28, 2021

(87) PCT Pub. No.: WO2020/087194
PCT Pub. Date: May 7, 2020

(65) Prior Publication Data
US 2022/0002353 A1    Jan. 6, 2022

(51) Int. Cl.
*C07K 14/195* (2006.01)
*C07K 1/13* (2006.01)
*C07K 1/22* (2006.01)

(52) U.S. Cl.
CPC .............. *C07K 14/195* (2013.01); *C07K 1/13* (2013.01); *C07K 1/22* (2013.01)

(58) Field of Classification Search
CPC ........... C07K 14/195; C07K 1/13; C07K 1/22
See application file for complete search history.

(56) References Cited

U.S. PATENT DOCUMENTS 8,053,635 B2 * 11/2011 Kok-Jacon ......... C12N 15/8245
                                                    800/278
10,745,675 B2 *  8/2020 Cote ..................... C12N 9/1051
2009/0064372 A1  3/2009 Kok-Jacon et al.

FOREIGN PATENT DOCUMENTS

CN    102757501 A    10/2012
RU    2428477 C2 *   9/2011

OTHER PUBLICATIONS

The Protein Man ("Protein tags: How to Choose?" blog post on https://info.gbiosciences.com/blog/protein-tags; Aug. 28, 2018, retrieved Feb. 26, 2024) (Year: 2018).*
Morimoto et al (Bioconjugate Chem. 2014, 25, 8, 1479-1491) (Year: 2014).*
Kimple et al (Curr Protoc Protein Sci. Sep. 24, 2013;73:9.9.1-9.9. 23) (Year: 2013).*
International Search Report for International Application No. PCT/CN2018/112303, dated Aug. 6, 2019, with English translation.
Kaseda et al., "A novel approach for purification of recombinant proteins using the dextrain-binding domain," FEBS Letters 500, FEBS 25020, 2001 (published Jun. 21, 2001), pp. 141-144.
NCBI, "KxYKxGKxW signal peptide domain-containing protein [Leuconostoc mesenteroides]," Protein, Locus WP_084014924, Apr. 6, 2020, 2 pages.
Suwannarangsee et al., "Search for a dextransucrase minimal motif involved in dextran binding," FEBS Letters 581, 2007 (published online Sep. 4, 2007), pp. 4675-4680.

* cited by examiner

*Primary Examiner* — Thomas J. Visone
*Assistant Examiner* — Georgiana C Reglas
(74) *Attorney, Agent, or Firm* — Birch, Stewart, Kolasch & Birch, LLP

(57) ABSTRACT

The application relates to a dextran affinity tag and use thereof. The present application provides an affinity tag, which is a segment of dextran binding domain, and can purify a target protein by its affinity with the dextran. The affinity tag of the present application has the advantages of more efficient in preparation and purification, and can be widely used in industrial applications that require protein purification processes.

11 Claims, 2 Drawing Sheets

Specification includes a Sequence Listing.

DEXTRAN AFFINITY TAG AND USE THEREOF

CROSS-REFERENCE TO RELATED APPLICATION

This application is the National Phase of PCT International Application No. PCT/CN2018/112303, filed on Oct. 29, 2018 which is hereby expressly incorporated by reference into the present application.

REFERENCE TO ELECTRONIC SEQUENCE LISTING

The application contains a Sequence Listing which has been submitted electronically in.txt format and is hereby incorporated by reference in its entirety. Said .XML copy, created on Apr. 28, 2021, is named "2021 Apr. 28-Sequence-Listing-5025-0383PUS1" and is 22,546 bytes in size. The sequence listing contained in this. XML file is part of the specification and is hereby incorporated by reference herein in its entirety.

BACKGROUND OF THE INVENTION

Field of the Invention

The present application is related to affinity chromatography for protein purification, specifically to the affinity tags used in affinity chromatography.

Description of the Prior Art

Recombinant protein produced by recombinant DNA technology has been widely used in the food, cosmetics, and pharmaceutical industries. The production process of recombinant protein can be divided into upstream, midstream, and downstream stages. The upstream stage is the research and development stage, which mainly involves the establishment of gene cloning and expression systems. The midstream stage is mainly for development of fermentation process and process scale-up. The downstream stage involves protein isolation and purification, quality control, and product packaging.

In the downstream stage of the recombinant protein production process, the efficiency of purification is critical to the manufacturing cost. In order to save costs, it is necessary to find the best purification strategy through repeated experiments. Common purification methods include ion exchange chromatography, hydrophobic-interaction chromatography, gel filtration chromatography, and affinity chromatography. Affinity chromatography uses a specific immobilized ligand to specifically interact with the protein itself or the affinity tag at the N-terminus or C-terminus of the protein to purify the protein, with the advantages of high recovery and simplified purification steps.

At present, a variety of affinity tags have been used in the purification of recombinant proteins, such as polyhistidine tag, cellulose binding domain, and chitin binding domain. Although affinity tags make protein purification more convenient, the cost of the commercial affinity resins used with the common affinity tags is still too high. Accordingly, there is still a need for more optional affinity tags in the field.

SUMMARY OF THE INVENTION

One object of the present application is to provide a novel recombinant protein that can be used as an affinity tag, providing more options for the field of affinity chromatography.

Another object of the present application is to provide a method for purifying protein using the affinity tag of the present application and having the advantage of reducing production costs.

To meet the above objects, the present application provides an affinity tag having an amino acid sequence of SEQ ID NO: 02; with the proviso that the amino acid sequence is not SEQ ID NO: 01.

The present application also provides an affinity tag having an amino acid sequence of SEQ ID NO: 10; with the proviso that the amino acid sequence is not SEQ ID NO: 01.

The present application also provides an isolated polynucleotide encoding an affinity tag; wherein the affinity tag has an amino acid sequence of SEQ ID NO: 02; with the proviso that the amino acid sequence of the affinity tag is not SEQ ID NO: 01.

The present application further provides an isolated polynucleotide encoding an affinity tag; wherein the affinity tag has an amino acid sequence of SEQ ID NO: 10; with the proviso that the amino acid sequence of the affinity tag is not SEQ ID NO: 01.

The present application also provides a recombinant protein, comprising the affinity tags mentioned above.

The present application further provides a method for purifying protein, comprising: (a) labeling a target protein with the affinity tag of the present application; wherein the labeled target protein is stored in a fluid; (b) mixing the fluid and a resin to form a mixture, and applying the mixture onto a column; wherein the resin contains dextran; (c) eluting the column with a washing solution to obtain the target protein from the resin; wherein the washing solution contains dextran.

DETAILED DESCRIPTION OF THE EMBODIMENTS

Figure 1:
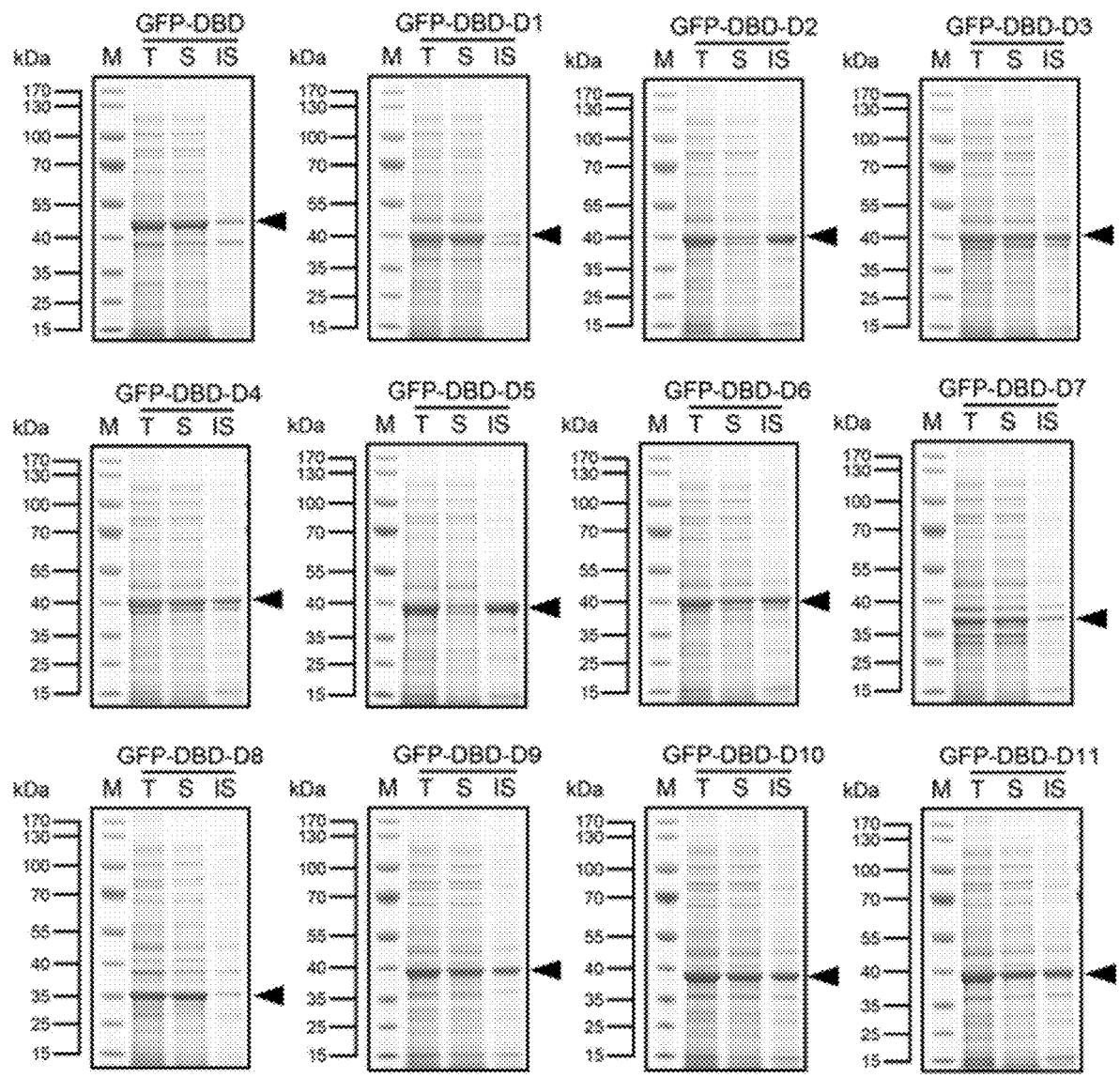
FIG. 1 shows the result of a protein electrophoresis indicating the induced expression of a recombinant fusion protein (Example 2 of the present application).

The description herein is only exemplary and explanatory, and is not intended to limit the claimed invention. The technical and scientific terms used herein should be understood as meanings commonly understood by those of ordinary skill in the art, unless clearly defined otherwise.

Unless the context clearly indicates otherwise, the singular form "a" or "an" in the description herein includes the plural meaning. Thus, for example, "a protein" refers to one or more proteins, and "a compound" refers to one or more compounds. The term "comprise", "comprises", "comprising", "include", "includes", and "including" are used interchangeable, and non-restrictive. It should be understood that in the description of each embodiment, when the term "comprising" is used, those skilled in the art will understand that in some specific cases, the term can be substituted by "consisting essentially of . . . " or "consisting of."

When a certain range of values is provided, unless the context clearly dictates otherwise, it should be understood that the integers in the numerical range and one tenth of each integer in the numerical range are between the upper and lower limits of the range, and any other stated values or intermediate values within this range are all covered by the claimed invention.

All documents, patents, patent applications, and other documents cited in the present application are fully incorporated herein as references, and their contents are as pointed out in each independent document, patent, patent application, or other document, which are fully incorporated herein as references.

Definition

The term "tag/affinity tag" used herein refers to a molecule that can be bound to a target protein for purification of the target protein. In a feasible embodiment, the tag is combined with the target protein to form a recombinant protein. The term "label" used herein is used to describe the binding relationship between a tag and a target protein. In a feasible embodiment, the tag is labeled with (i.e., bound to) the N-terminus of the target protein; in another feasible embodiment, the tag is labeled with (i.e., bound to) the C-terminus of the target protein.

As used herein, "dextran binding ability" refers to that the designated substance has the affinity to form a bond with dextran. The term "dextran binding domain (DBD)" used herein refers to a domain that can form a bond with dextran in the dextransucrase structure. The term "a segment of DBD" used herein refers to a polypeptide chain or a protein that has the affinity to form a bond with dextran, but does not have the full length of dextran binding domain known in the art. For example, the full length of the dextran binding domain is shown as SEQ ID NO: 01.

As used herein, the term "polynucleotide" refers to a molecule composed of more than one nucleotides, which can be transcribed and/or translated into a polypeptide or protein with physiological activity.

As used herein, the term "encode/encoding" refers to the process by which the polynucleotide is transcribed and/or translated to produce a polypeptide, or to further form a protein. The phrase "an isolated polynucleotide encoding a segment of dextran binding domain" refers to that the polynucleotide is transcribed and/or translated to produce a segment of dextran binding domain. The encoding can be carried out in vivo or in vitro. The encoding can be carried out in homologous cells or heterologous cells.

As used herein, the term "isolated" refers to being separated from the original environment, and does not specifically refer to being in a free state. For example, an isolated polynucleotide refers to a polynucleotide that has been separated from its original genome and is in a free state or is further genetically engineered to be inserted into a plasmid.

The term "purification/purify" used herein refers to enriching a target molecule by increasing the content of the target molecule in an environment, or by reducing the content of non-target molecules in the environment to increase the concentration of the target molecule in the environment.

The first aspect of the claimed invention:

The first aspect of the claimed invention relates to an affinity tag. In an embodiment, the affinity tag has an amino acid sequence of SEQ ID NO: 02; with the proviso that the amino acid sequence is not SEQ ID NO: 01. In another embodiment, the affinity tag has an amino acid sequence of SEQ ID NO: 10; with the proviso that the amino acid sequence is not SEQ ID NO: 01.

The term "the affinity tag has an amino acid sequence of SEQ ID NO" mentioned above or a similar description refers to that the amino acid sequence of the affinity tag includes the indicated sequence, but is not limited to the indicated sequence. For example, the term "the affinity tag has an amino acid sequence of SEQ ID NO: 02" means that the amino acid sequence of the affinity tag includes SEQ ID NO: 02 (in a specific embodiment, it consists essentially of SEQ ID NO: 02), but those skilled in the art can modify the indicated sequence with general knowledge in the art based on their needs, so that the modified sequence includes sequences other than SEQ ID NO: 02. The claimed invention does not exclude an affinity tag of the claimed invention with one or more amino acids extending at the N-terminus or C-terminus of the affinity tag by those skilled in the art. The claimed invention also does not exclude an affinity tag of the claimed invention with other protein sequences extending at the N-terminus or C-terminus of the affinity tag by those skilled in the art based on their needs. For example, a fusion partner can be added to the N-terminus or C-terminus of SEQ ID NO: 02 (to form a recombinant fusion protein) to increase the solubility of the recombinant protein. Examples of the fusion partner include DsbC of *Escherichia coli*, MsyB of *E. coli*, FkIB of *E. coli*, and small ubiquitin-like modifier (SUMO) of *Saccharomyces cerevisiae*. In addition, other affinity tags such as His tag, Strep tag, and T7 tag can also be bound to the N-terminus or C-terminus of SEQ ID NO: 02. In this way, the antibodies corresponding to these affinity tags can be used to detect the expression of recombinant proteins (for example, applied to Western Blot). Unless the modified sequence is equivalent to SEQ ID NO: 01, it should still be within the scope of the claimed invention.

In an embodiment, the affinity tag has an affinity to form a bond with dextran. The affinity can be determined by observation under a fluorescence microscope, measurement of dissociation constant, or purification effect. Among them, in observation under a fluorescence microscope, DBD with fluorescent substance is applied onto a resin composed of dextran, and then the affinity is determined by fluorescence intensity. In measurement of dissociation constant, DBD is bound on a microplate, different concentrations of biotin-dextran solution are added to the reaction, the microplate is washed, and then extravidin-alkaline phosphatase is added for color reaction; the absorbance value versus the concentration of biotin-dextran solution is plotted, and dissociation constant is calculated with one-site saturation ligand-binding equation in SigmaPlot. In purification effect, protein with DBD is applied onto a resin composed of dextran, the protein is extracted, and then the affinity of the purified protein is determined by electrophoresis or concentration measurement of the purified protein.

The second aspect of the claimed invention:

The second aspect of the claimed invention relates to an isolated polynucleotide encoding an affinity tag; wherein the affinity tag has an amino acid sequence of SEQ ID NO: 02; with the proviso that the amino acid sequence of the affinity tag is not SEQ ID NO: 01.

In an embodiment, the isolated polynucleotide has a sequence of SEQ ID NO: 14; with the proviso that the sequence is not SEQ ID NO: 13. In another embodiment, the isolated polynucleotide has a sequence of SEQ ID NO: 22; with the proviso that the sequence is not SEQ ID NO: 13.

The term "the isolated polynucleotide has a sequence of SEQ ID NO" mentioned above or a similar description refers to that the sequence of the isolated polynucleotide includes the indicated sequence, but is not limited to the indicated sequence. For example, the term "the isolated polynucleotide has a sequence of SEQ ID NO: 14" means that the sequence of the isolated polynucleotide includes SEQ ID NO: 14, but those skilled in the art can modify the indicated sequence with general knowledge in the art based on their needs, so that the modified sequence includes sequences other than SEQ ID NO: 14. The modified sequence, unless it is equivalent to SEQ ID NO: 13, should still be within the scope of the claimed invention.

In an embodiment, the isolated polynucleotide is constructed in an expression cassette of an expression vector. In a feasible embodiment, the expression vector can be replicated in *E. coli*, lactic acid bacteria, *Bacillus subtilis*, or a combination thereof. In a feasible embodiment, the expression vector can be used for protein expression in a prokaryotic cell expression system; wherein the prokaryotic cell comprises *E. coli*, lactic acid bacteria, *B. subtilis*, or a combination thereof. In another feasible embodiment, the expression vector can be expressed in eukaryotic cells; wherein the eukaryotic cells include yeast, Chinese hamster ovary (CHO) cells, mouse myeloma NS0 cells, baby hamster kidney (BHK) cells, mouse myeloma SP2/0 cells, human embryonic kidney cells HEK 293 cell line, HEK 293 EBNA cell line, human retinal cell PER.C6® cell line, and African green monkey kidney cell COS-7 cell line, or a combination thereof.

The third aspect of the claimed invention:

The third aspect of the claimed invention relates to a recombinant protein comprising an affinity tag mentioned above. In an embodiment, the recombinant protein comprises a target protein and an affinity tag labeled to the target protein. The term "target protein" as used herein refers to a protein to be produced for experimental or commercial purposes. In an experimental embodiment, the target protein is a green fluorescent protein. In a feasible embodiment, the affinity tag is labeled to the N-terminus of the target protein. In another feasible embodiment, the affinity tag is labeled to the C-terminus of the target protein.

In a feasible embodiment, the recombinant protein is produced by a prokaryotic cell expression system; wherein the nucleotides encoding the target protein and the nucleotides encoding the affinity tag are constructed in an expression cassette of an expression vector by genetic engineering technology for production in the prokaryotic cell expression system. In a feasible embodiment, the prokaryotic cell comprises *E. coli*, lactic acid bacteria, *B. subtilis*, or a combination thereof. In another feasible embodiment, the expression vector can be expressed in eukaryotic cells; wherein the eukaryotic cells include yeast, CHO cells, NS0 cells, BHK cells, SP2/0 cells, HEK 293 cells, HEK 293 EBNA cells, PER.C6® cells, and COS-7 cells, or a combination thereof.

Feasibly, the recombinant protein can be used in the preparation of subunit vaccines; wherein the target protein is the antigen of the subunit vaccine, and the target protein is purified by the affinity tag of the present application, thereby improving the production efficiency of the subunit vaccine.

The fourth aspect of the claimed invention:

A method for purifying protein, comprising: (a) labeling a target protein with the affinity tag of the present application; wherein the labeled target protein is stored in a fluid; (b) mixing the fluid and a resin to form a mixture, and applying the mixture onto a column; wherein the resin contains dextran; (c) eluting the column with a washing solution to obtain the target protein from the resin; wherein the washing solution contains dextran.

In a feasible embodiment, the labeling is carried out by genetic engineering technology. Specifically, the nucleotide encoding the target protein and the nucleotide encoding the affinity tag are constructed in an expression cassette of an expression vector by genetic engineering technology for expression in prokaryotic cells or eukaryotic cells.

The fluid generally refers to an environment containing the target protein, for example, a buffer solution or a prokaryotic cell culture medium or eukaryotic cell culture medium for expressing the target protein. Although the fluid is mostly in a liquid form, it is not limited to a liquid form.

In a feasible embodiment, the mixing in step (b) refers to contacting the fluid with the resin by any physical means (such as stirring, vortexing, or shaking). Although it does not intend to be limited by any theory, in step (b), the affinity tag labeled to the target protein will bind to the dextran in the resin, thereby binding the target protein to the resin. In an embodiment, the column in step (b) is a polypropylene column (for example, a product sold by QIAGEN), which can hold the resin and the target protein bound to the resin.

In an embodiment, although it does not intend to be limited by any theory, in step (c), the washing solution contains dextran, so that when the column is washed with the washing solution, the dextran in the washing solution will compete with the dextran in the resin for binding with the target protein, thereby the target protein will be separated from the resin and eluted with the washing solution. In a feasible embodiment, the concentration of dextran in the washing solution is 0.1 to 0.5% (w/v). In a feasible embodiment, those skilled in the art may adjust the concentration of dextran in the resin and washing solution based on their needs and process conditions.

In a feasible embodiment, the pH of the washing solution is 6-8. More preferably, the pH can be adjusted according to actual operating conditions. In an embodiment, the resin is a resin containing dextran, such as Sephacryl™ S-300 HR, Sephacryl™ S-500 HR, Superdex G75, or Superdex G100.

The following paragraphs lists the embodiments of the claimed invention, which are intended to exemplarily illustrate the features of the claimed invention but not to limit its scope. Each embodiment and feature described in the present application should be understood as interchangeable and combinable with each embodiment contained therein.

The primers used in the examples are shown in Table 1.

TABLE 1

| Primer Name | Sequence (5' to 3') | SEQ ID NO |
|---|---|---|
| DBDKPNIF | GATATAGGTACCAATCAGTATTATCAATTA GCAGATGGTAAATAT | SEQ ID NO: 25 |
| DBDSALIR | CTGCAGGTCGACTTATGCTGACACAGCATT TCCATTATTATC | SEQ ID NO: 26 |

TABLE 1-continued

| Primer Name | Sequence (5' to 3') | SEQ ID NO |
|---|---|---|
| DBDBAMHIM1 | GATGCTATCATTGTGGACCCAGATACTAA CTTGAG | SEQ ID NO: 27 |
| DBDBAMHIM2 | CTCAAGTTAGTATCTGGGTCCACAATGATA GCATC | SEQ ID NO: 28 |
| GFPNDEIF | GATATACATATGGCTAGCAAAGGAGAAGA ACTTTTC | SEQ ID NO: 29 |
| GFPKPNIR | CTGCAGGGTACCTTTGTAGAGCTCATCCAT GCCATGTG | SEQ ID NO: 30 |
| DBD-D1KPNIF | GATATAGGTACCGCGAAAACAGGGTTTGT ATTGC | SEQ ID NO: 31 |
| DBD-M01 | GCATTGAAATAATAACTCAAGTTAGTATCT GGTTGCAATACAAACCCTGTTTTCG | SEQ ID NO: 32 |
| DBD-M02 | CCAGATACTAACTTGAGTTATTATTTCAAT GC | SEQ ID NO: 33 |
| DBD-M03 | AATTACCTTGATACTCGAAATAATCATTTT TTGGGTCCACAATGATAGCATCTT | SEQ ID NO: 34 |
| DBD-M04 | AAAAATGATTATTTCGAGTATCAAGGTAA TT | SEQ ID NO: 35 |
| DBD-M05 | CCTTTGATAAGTTGATAATTAGCATCTGTT AATACAGCGACACCTTGTGTTGCA | SEQ ID NO: 36 |
| DBD-M06 | TTAACAGATGCTAATTATCAACTTATCAAA GG | SEQ ID NO: 37 |
| DBD-M07 | CAGTGACTTCATCAAAATGTTGTAAGCTTA AATACCAATTACCTTGATACTCGAAATAAT | SEQ ID NO: 38 |
| DBD-M08 | AGCTTACAACATTTTGATGAAGTCACTG | SEQ ID NO: 39 |
| DBD-D6SALIR | CTGCAGGTCGACTTAACTTATTAAAGCACT ATCTTTTGTTTGTACACC | SEQ ID NO: 40 |
| DBD-M09 | CAGTGACTTCATCAAAATGTTGTAAGCTTT GCAATACAAACCCTGTTTTCG | SEQ ID NO: 41 |
| DBD-M10 | CAAATTGGTAAACCTTACCCTGAGCACGA CCACTATCATCTAACAACATATATTTACC | SEQ ID NO: 42 |
| DBD-M11 | GCTCAGGGTAAGGTTTACCAATTTG | SEQ ID NO: 43 |
| DBD-D9KPNIF | GATATAGGTACCGATGGTGTACTAAGATA CTTCGATCAAAAC | SEQ ID NO: 44 |
| DBD-D8SALIR | CTGCAGGTCGACTTAACTTATTAAAGCACT ATCTTTTGTTTGTACACC | SEQ ID NO: 45 |
| DBD-D11SALIR | CTGCAGGTCGACTTATTGGTAAACCTTACC CTGAGCACT | SEQ ID NO: 46 |
| T7 promoter | CACTATAGGGGAATTGTGAGCGG | SEQ ID NO: 47 |
| T7 terminator | GCTAGTTATTGCTCAGCGGTGG | SEQ ID NO: 48 |

Example 1: Construction of Expression Vector for Expressing the Target Protein and the Affinity Tag of the Present Application The purpose of this example is to construct different dextran binding domains (DBD) by recombinant DNA technology to find the most suitable affinity tags. In this example, *Leuconostoc mesenteroides* strain ATIT-08 isolated from kimchi was used as the source of the full-length DNA of the dextran binding domain. *E. coli* ECOS™ 9-5 (Yeastern, Taiwan, China) was used as the host cell for DNA cloning. *E. coli* BL21 (DE3) (Thermo, USA) was used as the host cell for protein expression. Both *E. coli* strains are cultivated in Luria-Bertani (LB) medium and added with 30 μg/mL Kanamycin or 1.5% (w/v) agar as needed. The deMan-Rogosa-Sharpe (MRS) medium (Merck, USA) was used for the cultivation of *L. mesenteroides*. Both the culture medium and agar were purchased from BD Company (USA).

*L. mesenteroides* strain ATIT-08 was inoculated into 5 mL of MRS liquid medium and cultured at 30° C. for 16 hours. The genomic DNA from the strain were extracted using DNA purification kit (Tissue & Cell Genomic DNA Purification kit; GMbiolab, Taiwan). Primer combination of DBDKPNIF/DBDSALIR (SEQ ID NO: 25 and SEQ ID NO:

26) was used to amplify DBD DNA. The 50 µL PCR reaction mixture contains 1×GDP-HiFi PCR buffer, 200 µM dNTPs, 1 µM primers, 200 ng *L. mesenteroides* genomic DNA, and 1 U GDP-HiFi DNA polymerase (Genedirex, USA). PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using PCR Clean Up Kit (GMbiolab, Taiwan, China).

CloneJET PCR Cloning Kit (Thermo, USA) was then used for gene cloning. The ligation mixture was transformed into *E. coli* ECOS™ 9-5. Transformants possibly containing insert DNA were screened by colony polymerase chain reaction (SEQ ID NO: 25/SEQ ID NO: 26). After recombinant plasmids of transformants containing insert DNA were confirmed by electrophoresis, the plasmids were extracted from the transformants and undergone DNA sequencing. The plasmid with the correct DNA sequence was named pJET-LCDBD.

Construction of DBD Fusion Expression Vector pET-DBD.

Since DBD DNA contains the BamHI restriction site commonly used in gene cloning, mutation primers are designed for the restriction site and the overlap extension polymerase chain reaction was used for site-directed mutagenesis. The procedure of point mutation is summarized as follows.

The plasmid pJET-LCDBD was used as a template, and DBDKPNIF/DBDBAMHIM2 (SEQ ID NO: 25/SEQ ID NO: 28) and DBDBAMHIM1/DBDSALIR (SEQ ID NO: 27 and SEQ ID NO: 26) primer sets were used to amplify DNA fragments. The 50 µL PCR reaction mixture contains 1×GDP-HiFi PCR buffer B, 200 µM dNTPs, 1 µM primers, 100 ng pJET-LCDBD, and 1 U GDP-HiFi DNA polymerase.

PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit (GMbiolab, Taiwan, China).

Next, the two recovered PCR products were used as templates, and the DBDKPNIF/DBDSALIR primer combination (SEQ ID NO: 25/SEQ ID NO: 26) was used to amplify DBD DNA fragment. PCR was run with the following procedure: 96° C. for 2 minutes (1 step); 94° C. for 15 seconds, 55° C. for 30 seconds, 68° C. for 1 minute (35 cycles); 68° C. for 5 minutes (1 step). After this step, DBD DNA with site-directed mutation was obtained and has a sequence of SEQ ID NO: 13, which encodes SEQ ID NO: 01.

After the PCR product was cut with KpnI and SalI, the DNA fragment was inserted into the plasmid pET29a (+) cut with the same restriction enzyme using T4 DNA ligase. The product plasmid was transformed into *E. coli* ECOS™ 9-5. Transformants possibly containing insert DNA were screened by colony polymerase chain reaction (SEQ ID NO: 25/SEQ ID NO: 26). After recombinant plasmids of transformants containing insert DNA were confirmed by electrophoresis, the plasmids were extracted from the transformants and undergone DNA sequencing. The plasmid with the correct DNA sequence was named pET-DBD.

Construction of Green Fluorescent Protein Expression Vector pET-GFP and Green Fluorescent Protein-DBD Fusion Expression Vector pET-GFP-DBD.

Green fluorescent protein was used as the target protein in the examples of the present application. The GFPNDEIF/GFPKPNIR primer combination (SEQ ID NO: 29/SEQ ID NO: 30) was used to amplify the enhanced green fluorescent protein (GFP) gene. The 50 µL PCR reaction mixture contains 1×GDP-HiFi PCR buffer, 200 µM dNTPs, 1 µM primers, 100 ng pBRLP-8-P23-GFPT, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using PCR Clean Up Kit.

After the PCR product was cut with NdeI and KpnI, the DNA fragment was inserted into the plasmid pET29a (+) or the plasmid pET-DBD cut with the same restriction enzyme using T4 DNA ligase. The product plasmid was transformed into *E. coli* ECOS™ 9-5. Transformants possibly containing insert DNA were screened by colony polymerase chain reaction (SEQ ID NO: 29/SEQ ID NO: 30). After recombinant plasmids of transformants containing insert DNA were confirmed by electrophoresis, the plasmids were extracted from the transformants and undergone DNA sequencing. The pET29a (+) plasmid containing the GFP gene was named pET-GFP. The pET-DBD plasmid containing the GFP gene was named pET-GFP-DBD.

The Deletion Mutation of DBD.

1. DBD-D1:

The DBD-D1KPNIF/DBDSALIR primer combination (SEQ ID NO: 31/SEQ ID NO: 26) was used to amplify the DBD-D1 DNA. The 50 µL PCR reaction mixture contains 1×GDP-HiFi PCR buffer, 200 µM dNTPs, 1 µM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. The PCR products was the affinity tag DBD-D1 of the present application and has a sequence of SEQ ID NO: 14, which encodes SEQ ID NO: 02.

2. DBD-D2, DBD-D3, DBD-D4, DBD-D5, DBD-D7, and DBD-D8:

The DNA fragments were amplified using the primer sets shown in Table 2 below. The 50 µL PCR reaction mixture contains 1×GDP-HiFi PCR buffer B, 200 µM dNTPs, 1 µM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. Two PCR products were prepared for experiment samples of each affinity tag.

TABLE 2

| Sample | Primer Name and Sequence Number | |
|---|---|---|
| DBD-D2 | Primer set 1 | DBDKPNIF/DBD-M01 (SEQ ID NO: 25/SEQ ID NO: 32) |
| | Primer set 2 | DBD-M02/DBDSALIR (SEQ ID NO: 33/SEQ ID NO: 26) |

TABLE 2-continued

| Sample | Primer Name and Sequence Number | |
| --- | --- | --- |
| DBD-D3 | Primer set 1 | DBDKPNIF/DBD-M03 (SEQ ID NO: 25/SEQ ID NO: 34) |
| | Primer set 2 | DBD-M04/DBDSALIR (SEQ ID NO: 35/SEQ ID NO: 26) |
| DBD-D4 | Primer set 1 | DBDKPNIF/DBD-M05 (SEQ ID NO: 25/SEQ ID NO: 36) |
| | Primer set 2 | DBD-M06/DBDSALIR (SEQ ID NO: 37/SEQ ID NO: 26) |
| DBD-D5 | Primer set 1 | DBDKPNIF/DBD-M07 (SEQ ID NO: 25/SEQ ID NO: 38) |
| | Primer set 2 | DBD-M08/DBDSALIR (SEQ ID NO: 39/SEQ ID NO: 26) |
| DBD-D7 | Primer set 1 | DBDKPNIF/DBD-M09 (SEQ ID NO: 25/SEQ ID NO: 41) |
| | Primer set 2 | DBD-M08/DBDSALIR (SEQ ID NO: 39/SEQ ID NO: 26) |
| DBD-D8 | Primer set 1 | DBDKPNIF/DBD-M10 (SEQ ID NO: 25/SEQ ID NO: 42) |
| | Primer set 2 | DBD-M11/DBDSALIR (SEQ ID NO: 43/SEQ ID NO: 26) |

The two recovered PCR products were used as templates, and DBDKPNIF/DBDSALIR (SEQ ID NO: 25/SEQ ID NO: 26) primer combination was used for gene amplification. PCR was run with the following procedure: 96° C. for 2 minutes (1 step); 94° C. for 15 seconds, 55° C. for 30 seconds, 68° C. for 1 minute (35 cycles); 68° C. for 5 minutes (1 step). After this step, the corresponding DBD-D2, DBD-D3, DBD-D4, DBD-D5, DBD-D7, and DBD-D8 fragments were obtained respectively. The PCR products were recovered using PCR Clean Up Kit.

The affinity tag DBD-D2 of the present application has a sequence of SEQ ID NO: 15, which encodes SEQ ID NO: 03.

The affinity tag DBD-D3 of the present application has a sequence of SEQ ID NO: 16, which encodes SEQ ID NO: 04.

The affinity tag DBD-D4 of the present application has a sequence of SEQ ID NO: 17, which encodes SEQ ID NO: 05.

The affinity tag DBD-D5 of the present application has a sequence of SEQ ID NO: 18, which encodes SEQ ID NO: 06.

The affinity tag DBD-D7 of the present application has a sequence of SEQ ID NO: 20, which encodes SEQ ID NO: 08.

The affinity tag DBD-D8 of the present application has a sequence of SEQ ID NO: 21, which encodes SEQ ID NO: 09.

3. DBD-D6:

The DBDKPNIF/DBD-D6SALIR (SEQ ID NO: 25/SEQ ID NO: 40) primer combination was used to amplify DBD-D6 DNA. The 50 μL PCR reaction mixture contains 1×GDP-HiFi PCR buffer, 200 μM dNTPs, 1 μM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. The PCR products was the affinity tag DBD-D6 of the present application and has a sequence of SEQ ID NO: 19, which encodes SEQ ID NO: 07.

4. DBD-D9:

The DBD-D9KPNIF/DBDSALIR (SEQ ID NO: 44/SEQ ID NO: 26) primer combination was used to amplify DBD-D9 DNA. The 50 μL PCR reaction mixture contains 1×GDP-HiFi PCR buffer, 200 μM dNTPs, 1 μM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. The PCR products was the affinity tag DBD-D9 of the present application and has a sequence of SEQ ID NO: 22, which encodes SEQ ID NO: 10.

5. DBD-D10:

The DBD-D1KPNIF/DBD-D8SALIR (SEQ ID NO: 31/SEQ ID NO: 45) primer combination was used to amplify the DBD-D10 DNA. The 50 μL PCR reaction mixture contains 1×GDP-HiFi PCR buffer, 200 μM dNTPs, 1 μM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. The PCR products was the affinity tag DBD-D10 of the present application and has a sequence of SEQ ID NO: 23, which encodes SEQ ID NO: 11.

6. DBD-D11:

The DBD-D1KPNIF/DBD-D11SALIR (SEQ ID NO: 31/SEQ ID NO: 46) primer combination was used to amply DBD-D11 DNA. The 50 μL PCR reaction mixture contains 1×GDP-HiFi PCR buffer, 200 μM dNTPs, 1 μM primers, 100 ng pET-GFP-DBD, and 1 U GDP-HiFi DNA polymerase. PCR was run with the following procedure: 96° C. for 2 minutes (1 step); 94° C. for 15 seconds, 55° C. for 30 seconds, 68° C. for 30 seconds (35 cycles); 68° C. for 5 minutes (1 step). After the PCR is completed, and the sizes of the DNA fragments were confirmed, the PCR products were recovered using Gel-M™ gel extraction system kit. The PCR products was the affinity tag DBD-D11 of the present application and has a sequence of SEQ ID NO: 24, which encodes SEQ ID NO: 12.

Example 2: Purification of the Target Protein by the Affinity Tag of the Present Application Construction of the Fusion Expression Vector of Green Fluorescent Protein Deletion Mutant DBD.

After the DNA of deletion mutant DBD was cut with KpnI and SalI, the DNA fragment was inserted into the pET-GFP cut with the same restriction enzyme using T4 DNA ligase. The product plasmid was transformed into E. coli ECOS™ 9-5 Transformants possibly containing insert DNA were screened by colony polymerase chain reaction (T7 promoter/T7 terminator (SEQ ID NO: 47/SEQ ID NO: 48)). After recombinant plasmids of transformants containing insert DNA were confirmed by electrophoresis, the plasmids were extracted from the transformants and undergone DNA sequencing. The plasmid with the correct DNA sequence was named pET-GFP-DBD-D1~pET-GFP-DBD-D11.

Transformation of Fusion Protein Expression Vector and Induced Expression of Recombinant Fusion Protein.

The fusion protein expression vector pET-GFP-DBD and pET-GFP-DBD-D1~pET-GFP-DBD-D11 were transformed into E. coli BL21 (DE3). A single colony was selected and inoculated into 5 mL LB medium containing kanamycin (a final concentration of 30 µg/mL) and cultured at 25° C. and 180 rpm. After overnight incubation, 100 µL of the culture was added into 10 mL LB medium containing kanamycin (a final concentration of 30 µg/mL) and cultured with shaking at 37° C. and 180 rpm to that the $OD_{600}$ value reaches about 0.4 to 0.6. Then, 0.1 mM isopropyl β-D-1-thiogalactopyranoside (IPTG) was added to the culture, and induce expression of the recombinant protein was carried out at 25° C. After 4 hours of induction, 2 mL of the bacterium was centrifuged (20,630×g, 5 minutes, 4° C.), the pellet was collected and divided into soluble protein and insoluble protein (i.e., solubility). Soluble expression of the recombinant fusion protein was checked by protein electrophoresis. ImageQuant TL software (GE, USA) was used to analyze the percentage of recombinant protein in the total protein in the gel, which is the expression percentage.

The results of protein electrophoresis (FIG. 1) showed that all the fusion proteins prepared in Example 1 were expressed normally, although the expression levels of GFP-DBD-D7, GFP-DBD-D9 and GFP-DBD-D10 were relatively low. In other words, the affinity tag of the present application does not affect the expression of the target protein. Based on the results in FIG. 1, the affinity tags of the present application affect the solubility of the fusion protein. Specifically, GFP-DBD, GFP-DBD-D1, and GFP-DBD-D8 are mainly soluble proteins; GFP-DBD-D2 and GFP-DBD-D5 are mainly insoluble proteins (Table 3).

TABLE 3

| Host | Concentration of the target protein (mg/mL) | Solubility percentage (%) |
|---|---|---|
| BL21 (DE3)(pET-GFP-DBD) | 0.096 | 81.90 |
| BL21 (DE3)(pET-GFP-DBD-D1) | 0.083 | 93.41 |
| BL21 (DE3)(pET-GFP-DBD-D2) | 0.083 | 39.66 |
| BL21 (DE3)(pET-GFP-DBD-D3) | 0.084 | 66.67 |
| BL21 (DE3)(pET-GFP-DBD-D4) | 0.079 | 65.88 |
| BL21 (DE3)(pET-GFP-DBD-D5) | 0.092 | 21.21 |
| BL21 (DE3)(pET-GFP-DBD-D6) | 0.093 | 55.66 |
| BL21 (DE3)(pET-GFP-DBD-D7) | 0.055 | 65.22 |
| BL21 (DE3)(pET-GFP-DBD-D8) | 0.084 | 79.80 |
| BL21 (DE3)(pET-GFP-DBD-D9) | 0.068 | 60.44 |
| BL21 (DE3)(pET-GFP-DBD-D10) | 0.071 | 58.76 |
| BL21 (DE3)(pET-GFP-DBD-D11) | 0.097 | 56.03 |

Purification of Recombinant GFP-DBD or GFP-DBD Deletion Mutant Fusion Protein.

The soluble protein fraction obtained by inducing expression at 25° C. was added to 100 µL of Sephacryl™ S-300 HR resin (GE Healthcare, Sweden). After mixing for 30 minutes, the mixture was put into a spin column. The spin column was further placed in a collection tube, and the effluent was discarded after centrifugation (100×g, 1 minute). The resin was washed with 1.2 mL lysis buffer (50 mM sodium phosphate, 0.05 g/L $CaCl_2$), 0.3 M NaCl, 1% triton X-100, pH 7.2) (used as a washing buffer), and then the recombinant fusion protein (100 µL/tube) in the resin was extracted with 200 µL elution buffer (50 mM sodium phosphate, 0.5% dextran, pH 7.2). The purification of the recombinant fusion protein was confirmed by protein electrophoresis.

Figure 2:
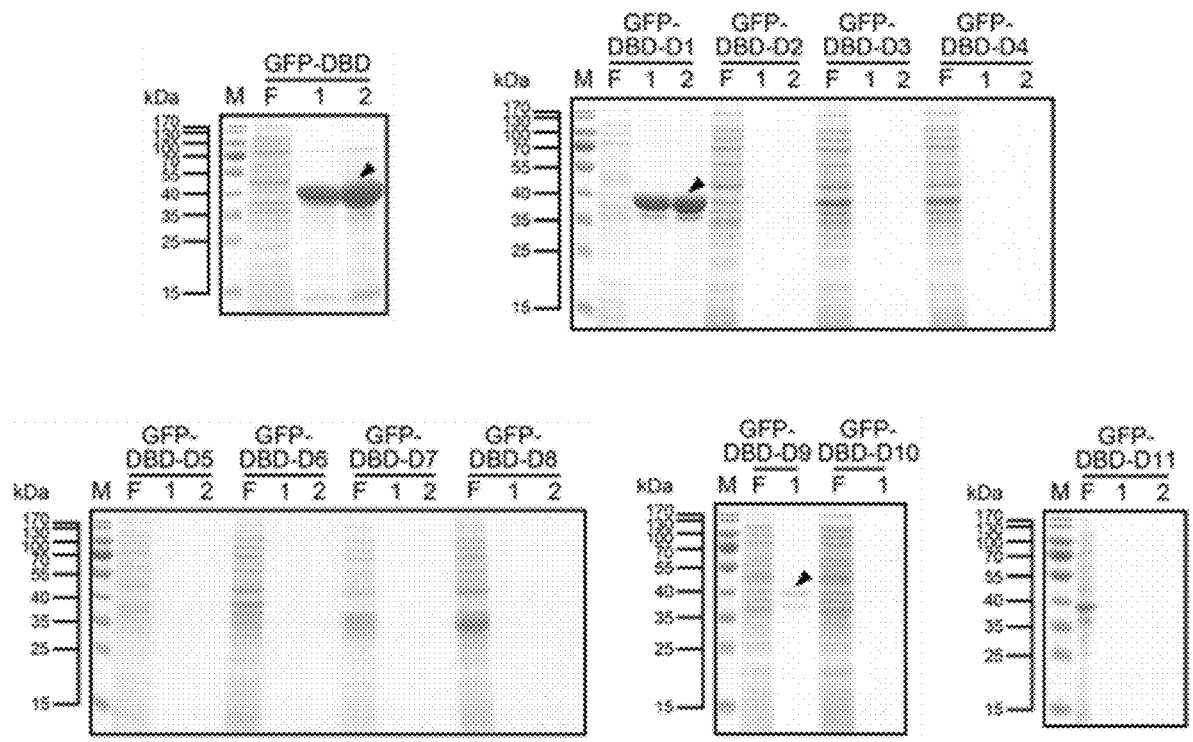
FIG. 2 shows the result of a protein electrophoresis showing the purification results of the recombinant GFP-DBD or GFP-DBD deletion mutant fusion protein (Example 2 of the present application).

The results of protein electrophoresis showed (FIG. 2) that among the affinity tags constructed in Example 1, only the fusion proteins of DBD, DBD-D1, and DBD-9 can bind to Sephacryl™ S-300 HR resin. The binding capacity of DBD-D1 to resin is better than that of DBD-9, and DBD-D1 shows similar affinity to DBD. This result indicates that the present application successfully tested the DBD fragments that can retain the affinity with dextran. That is, there is no need to express the full length of DBD, and the specific fragments can be used as affinity tags, which is more efficient in terms of protein expression. In addition, the results of the present application also indicate that not every DBD fragment can be used as an affinity tag, which is not easily foreseen from the sequence of the DBD before the present application.

Example 3: Comparison of the Affinity Tags of the Present Application with the Conventional His-Tag Expression and Purification of GFP-His Tag.

E. coli BL21 (DE3) (pET-GFP) was inoculated in 50 mL LB medium containing kanamycin (a final concentration of 30 µg/mL), and culture with shaking at 37° C. and 180 rpm to that the $OD_{600}$ value reaches about 0.4 to 0.6. Then 0.1 mM IPTG was added into the culture, and the recombinant protein was induced to express at 25° C. After 4 hours of induction, the cells were collected by centrifugation (7,354× g, 30 minutes, 4° C.), and the cells were suspended in 40 mL of lysis buffer (20 mM sodium phosphate, 500 mM NaCl, 1% triton X-100, pH 7.4) and sonicated. The sonicated bacteria were then centrifuged (39,191×g, 30 minutes, 4° C.), and the supernatant was collected. Two (2) mL of Ni Sepharose™ excel resin (GE Healthcare, Sweden) was added to the supernatant and shake at 160 rpm for 30 minutes at 4° C. to mix the supernatant with the resin. The supernatant containing resin was added into a polypropylene column (QIAGEN, Germany), and the effluent was discarded. Sixty (60) mL of washing buffer (20 mM sodium phosphate, 500 mM NaCl, 30 mM imidazole, pH 7.4) was used to remove non-specifically bound proteins on the resin. Finally, 25 mL of elution buffer (20 mM sodium phosphate, 500 mM NaCl, 250 mM imidazole, pH 7.4) was used to extract the recombinant protein on the resin. The purification of the recombinant fusion protein was confirmed by protein electrophoresis.

Expression and Purification of GFP-DBD and GFP-DBD-D1.

E. coli BL21 (DE3) (pET-GFP-DBD) or E. coli BL21 (DE3) (pET-GFP-DBD-D1) was inoculated in 50 mL LB medium containing kanamycin (a final concentration of 30 µg/mL) and cultured with shaking at 37° C. and 180 rpm to that the $OD_{600}$ value reaches about 0.4 to 0.6. Then 0.1 mM IPTG was added to the culture, and the recombinant protein was induced to express at 25° C. After 4 hours of induction, the cells were collected by centrifugation (7,354×g, 30 minutes, 4° C.) and then suspended in 40 mL of lysis buffer (50 mM sodium phosphate, 0.05 g/L $CaCl_2$, 0.3 M NaCl, 1% triton X-100, pH 7.2) and sonicated. The sonicated bacteria were then centrifuged (39,191×g, 30 minutes, 4° C.), and the supernatant was collected. Two (2) mL of Sephacryl™ S-300 HR resin was added to the supernatant and shake at 160 rpm for 30 minutes at 4° C. to mix the supernatant with the resin. The supernatant containing resin was added into a polypropylene column (QIAGEN, Germany), and the effluent was discarded. Sixty (60) mL of lysis buffer (used as washing buffer) was used to remove non-specifically bound proteins on the resin. Finally, 25 mL of elution buffer (50 mM sodium phosphate, 0.5% dextran, pH 7.2) was used to extract the recombinant protein on the resin. The purification of the recombinant fusion protein was confirmed by protein electrophoresis.

Figure 3:
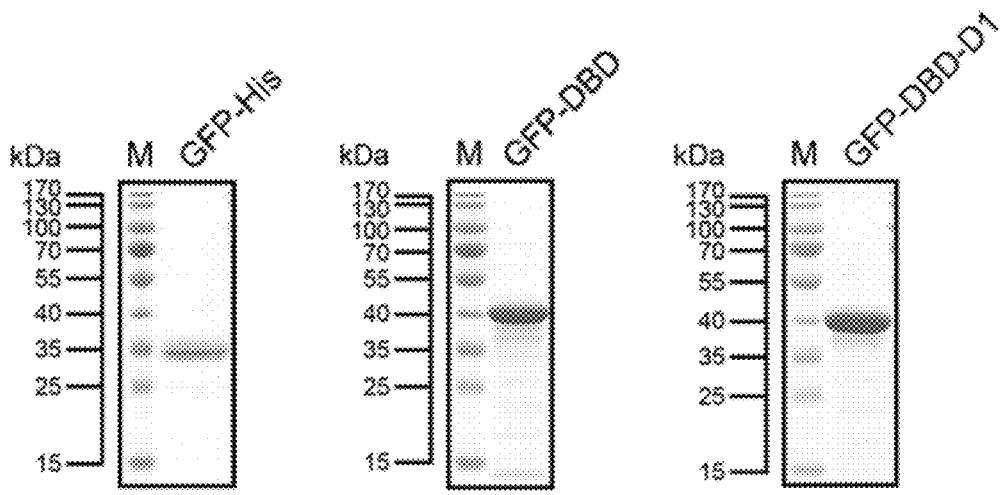
FIG. 3 shows the result of a protein electrophoresis indicating the purification results of GFP-His-tag, GFP-DBD, and GFP-DBD-D1 (Example 3 of the present application).

The results of protein electrophoresis indicate that all the recombinant GFP with affinity tags can be purified (FIG. 3), and the affinity tags of the present application can indeed be used for protein purification. In addition, the yield of DBD-D1 of the present application is the highest, surpassing the His tag commonly used in the field, and is also better than the full length of DBD (Table 4).

TABLE 4

| Recombinant Protein | Average target protein obtained per liter of bacterium (mg/L) | Molecule Number of Target Protein |
| --- | --- | --- |
| GFP-His | 55.85 | $1.18 \times 10^{18}$ |
| GFP-DBD | 80.28 | $1.16 \times 10^{18}$ |
| GFP-DBD-D1 | 89.35 | $1.43 \times 10^{18}$ |

Accordingly, the affinity tag of the present application is not only more efficient in terms of protein expression, but more efficient in terms of purification efficiency.

What is claimed is:

1. An affinity tag consisting of the amino acid sequence of SEQ ID NO: 02.

2. An isolated polynucleotide encoding an affinity tag, wherein the affinity tag consists of the amino acid sequence of SEQ ID NO: 02.

3. The isolated polynucleotide of claim 2, wherein the isolated polynucleotide consists of the nucleic acid has a sequence of SEQ ID NO: 14.

4. A recombinant protein, consisting of a target protein and an affinity tag of claim 1.

5. The recombinant protein of claim 4, wherein the affinity tag is labeled to the N-terminus of the target protein.

6. The recombinant protein of claim 4, wherein the affinity tag is labeled to the C-terminus of the target protein.

7. A method for purifying protein, comprising:
(a) labeling a target protein with the affinity tag of claim 1; wherein the labeled target protein is stored in a fluid;
(b) mixing the fluid and a resin to form a mixture, and applying the mixture onto a column; wherein the resin contains dextran;
(c) eluting the column with a washing solution to obtain the target protein from the resin; wherein the washing solution contains dextran.

8. The method of claim 7, wherein the labeling is carried out by genetic engineering technology.

9. The method of claim 7, wherein a concentration of the dextran in the washing solution is 0.1 to 0.5% (w/v).

10. The method of claim 7, wherein a pH of the washing solution is 6-8.

11. The method of claim 7, wherein the column is a polypropylene column.

* * * * *

SEQUENCE LISTING

<160> NUMBER OF SEQ ID NOS: 48

<210> SEQ ID NO 1
<211> LENGTH: 131
<212> TYPE: PRT
<213> ORGANISM: Leuconostoc mesenteroides

<400> SEQUENCE: 1

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Asp Gly Val Leu Arg
            20                  25                  30

Tyr Phe Asp Gln Asn Gly Glu Gln Val Lys Asp Ala Ile Ile Val Asp
        35                  40                  45

Pro Asp Thr Asn Leu Ser Tyr Tyr Phe Asn Ala Thr Gln Gly Val Ala
    50                  55                  60

Val Lys Asn Asp Tyr Phe Glu Tyr Gln Gly Asn Trp Tyr Leu Thr Asp
65                  70                  75                  80

Ala Asn Tyr Gln Leu Ile Lys Gly Phe Lys Ala Val Asp Asp Ser Leu
                85                  90                  95

Gln His Phe Asp Glu Val Thr Gly Val Gln Thr Lys Asp Ser Ala Leu
            100                 105                 110

Ile Ser Ala Gln Gly Lys Val Tyr Gln Phe Asp Asn Asn Gly Asn Ala
        115                 120                 125

Val Ser Ala
    130

<210> SEQ ID NO 2
<211> LENGTH: 112
<212> TYPE: PRT
<213> ORGANISM: Artificial Sequence
<220> FEATURE:
<223> OTHER INFORMATION: peptide

<400> SEQUENCE: 2

Ala Lys Thr Gly Phe Val Leu Gln Asp Gly Val Leu Arg Tyr Phe Asp
1               5                   10                  15

Gln Asn Gly Glu Gln Val Lys Asp Ala Ile Ile Val Asp Pro Asp Thr
            20                  25                  30

Asn Leu Ser Tyr Tyr Phe Asn Ala Thr Gln Gly Val Ala Val Lys Asn
        35                  40                  45

Asp Tyr Phe Glu Tyr Gln Gly Asn Trp Tyr Leu Thr Asp Ala Asn Tyr
    50                  55                  60

Gln Leu Ile Lys Gly Phe Lys Ala Val Asp Asp Ser Leu Gln His Phe
65                  70                  75                  80

Asp Glu Val Thr Gly Val Gln Thr Lys Asp Ser Ala Leu Ile Ser Ala
            85                  90                  95

Gln Gly Lys Val Tyr Gln Phe Asp Asn Asn Gly Asn Ala Val Ser Ala
            100                 105                 110

<210> SEQ ID NO 3
<211> LENGTH: 110
<212> TYPE: PRT
<213> ORGANISM: Artificial Sequence
<220> FEATURE:
<223> OTHER INFORMATION: peptide

<400> SEQUENCE: 3

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Pro Asp Thr Asn Leu
            20                  25                  30

Ser Tyr Tyr Phe Asn Ala Thr Gln Gly Val Ala Val Lys Asn Asp Tyr
            35                  40                  45

Phe Glu Tyr Gln Gly Asn Trp Tyr Leu Thr Asp Ala Asn Tyr Gln Leu
    50                  55                  60

Ile Lys Gly Phe Lys Ala Val Asp Asp Ser Leu Gln His Phe Asp Glu
65                  70                  75                  80

Val Thr Gly Val Gln Thr Lys Asp Ser Ala Leu Ile Ser Ala Gln Gly
            85                  90                  95

Lys Val Tyr Gln Phe Asp Asn Asn Gly Asn Ala Val Ser Ala
            100                 105                 110

<210> SEQ ID NO 4
<211> LENGTH: 115
<212> TYPE: PRT
<213> ORGANISM: Artificial Sequence
<220> FEATURE:
<223> OTHER INFORMATION: peptide

<400> SEQUENCE: 4

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Asp Gly Val Leu Arg
            20                  25                  30

Tyr Phe Asp Gln Asn Gly Glu Gln Val Lys Asp Ala Ile Ile Val Asp
            35                  40                  45

Pro Lys Asn Asp Tyr Phe Glu Tyr Gln Gly Asn Trp Tyr Leu Thr Asp
    50                  55                  60

Ala Asn Tyr Gln Leu Ile Lys Gly Phe Lys Ala Val Asp Asp Ser Leu
65                  70                  75                  80

Gln His Phe Asp Glu Val Thr Gly Val Gln Thr Lys Asp Ser Ala Leu
            85                  90                  95

Ile Ser Ala Gln Gly Lys Val Tyr Gln Phe Asp Asn Asn Gly Asn Ala
            100                 105                 110

Val Ser Ala
        115

<210> SEQ ID NO 5
<211> LENGTH: 119
<212> TYPE: PRT
<213> ORGANISM: Artificial Sequence
<220> FEATURE:
<223> OTHER INFORMATION: peptide

```
<400> SEQUENCE: 5

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Asp Gly Val Leu Arg
            20                  25                  30

Tyr Phe Asp Gln Asn Gly Glu Gln Val Lys Asp Ala Ile Ile Val Asp
        35                  40                  45

Pro Asp Thr Asn Leu Ser Tyr Tyr Phe Asn Ala Thr Gln Gly Val Ala
    50                  55                  60

Val Leu Thr Asp Ala Asn Tyr Gln Leu Ile Lys Gly Phe Lys Ala Val
65                  70                  75                  80

Asp Asp Ser Leu Gln His Phe Asp Glu Val Thr Gly Val Gln Thr Lys
                85                  90                  95

Asp Ser Ala Leu Ile Ser Ala Gln Gly Lys Val Tyr Gln Phe Asp Asn
            100                 105                 110

Asn Gly Asn Ala Val Ser Ala
        115

<210> SEQ ID NO 6
<211> LENGTH: 115
<212> TYPE: PRT
<213> ORGANISM: Artificial Sequence
<220> FEATURE:
<223> OTHER INFORMATION: peptide

<400> SEQUENCE: 6

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Asp Gly Val Leu Arg
            20                  25                  30

Tyr Phe Asp Gln Asn Gly Glu Gln Val Lys Asp Ala Ile Ile Val Asp
        35                  40                  45

Pro Asp Thr Asn Leu Ser Tyr Tyr Phe Asn Ala Thr Gln Gly Val Ala
    50                  55                  60

Val Lys Asn Asp Tyr Phe Glu Tyr Gln Gly Asn Trp Tyr Leu Ser Leu
65                  70                  75                  80

Gln His Phe Asp Glu Val Thr Gly Val Gln Thr Lys Asp Ser Ala Leu
                85                  90                  95

Ile Ser Ala Gln Gly Lys Val Tyr Gln Phe Asp Asn Asn Gly Asn Ala
            100                 105                 110

Val Ser Ala
        115

<210> SEQ ID NO 7
<211> LENGTH: 114
<212> TYPE: PRT
<213> ORGANISM: Artificial Sequence
<220> FEATURE:
<223> OTHER INFORMATION: peptide

<400> SEQUENCE: 7

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Asp Gly Val Leu Arg
            20                  25                  30

Tyr Phe Asp Gln Asn Gly Glu Gln Val Lys Asp Ala Ile Ile Val Asp
        35                  40                  45
```

Pro Asp Thr Asn Leu Ser Tyr Tyr Phe Asn Ala Thr Gln Gly Val Ala
    50                  55                  60

Val Lys Asn Asp Tyr Phe Glu Tyr Gln Gly Asn Trp Tyr Leu Thr Asp
65                  70                  75                  80

Ala Asn Tyr Gln Leu Ile Lys Gly Phe Lys Ala Val Asp Asp Ser Leu
                85                  90                  95

Gln His Phe Asp Glu Val Thr Gly Val Gln Thr Lys Asp Ser Ala Leu
                100                 105                 110

Ile Ser

<210> SEQ ID NO 8
<211> LENGTH: 64
<212> TYPE: PRT
<213> ORGANISM: Artificial Sequence
<220> FEATURE:
<223> OTHER INFORMATION: peptide

<400> SEQUENCE: 8

Asn Gln Tyr Tyr Gln Leu Ala Asp Gly Lys Tyr Met Leu Leu Asp Asp
1               5                   10                  15

Ser Gly Arg Ala Lys Thr Gly Phe Val Leu Gln Ser Leu Gln His Phe
                20                  25                  30

Asp Glu Val Thr Gly Val Gln Thr Lys Asp Ser Ala Leu Ile Ser Ala
                35                  40                  45

Gln Gly Lys Val Tyr Gln Phe Asp Asn Gly Asn Ala Val Ser Ala
            50                  55                  60

<210> SEQ ID NO 9
<211> LENGTH: 36
<212> TYPE: PRT
<213> ORGANISM: Artificial Sequence
<220> FEATURE:
<223> OTHER INFORMATION: peptide

<400> SEQUENCE: 9

Asn Gln Tyr Tyr Gln Leu Ala Asp Gly Lys Tyr Met Leu Leu Asp Asp
1               5                   10                  15

Ser Gly Arg Ala Gln Gly Lys Val Tyr Gln Phe Asp Asn Gly Asn
                20                  25                  30

Ala Val Ser Ala
            35

<210> SEQ ID NO 10
<211> LENGTH: 104
<212> TYPE: PRT
<213> ORGANISM: Artificial Sequence
<220> FEATURE:
<223> OTHER INFORMATION: peptide

<400> SEQUENCE: 10

Asp Gly Val Leu Arg Tyr Phe Asp Gln Asn Gly Glu Gln Val Lys Asp
1               5                   10                  15

Ala Ile Ile Val Asp Pro Asp Thr Asn Leu Ser Tyr Tyr Phe Asn Ala
                20                  25                  30

Thr Gln Gly Val Ala Val Lys Asn Asp Tyr Phe Glu Tyr Gln Gly Asn
                35                  40                  45

Trp Tyr Leu Thr Asp Ala Asn Tyr Gln Leu Ile Lys Gly Phe Lys Ala
            50                  55                  60

Val Asp Asp Ser Leu Gln His Phe Asp Glu Val Thr Gly Val Gln Thr

```
                    65                  70                  75                  80
Lys Asp Ser Ala Leu Ile Ser Ala Gln Gly Lys Val Tyr Gln Phe Asp
                85                  90                  95

Asn Asn Gly Asn Ala Val Ser Ala
            100

<210> SEQ ID NO 11
<211> LENGTH: 95
<212> TYPE: PRT
<213> ORGANISM: Artificial Sequence
<220> FEATURE:
<223> OTHER INFORMATION: peptide

<400> SEQUENCE: 11

Ala Lys Thr Gly Phe Val Leu Gln Asp Gly Val Leu Arg Tyr Phe Asp
1               5                   10                  15

Gln Asn Gly Glu Gln Val Lys Asp Ala Ile Ile Val Asp Pro Asp Thr
                20                  25                  30

Asn Leu Ser Tyr Tyr Phe Asn Ala Thr Gln Gly Val Ala Val Lys Asn
            35                  40                  45

Asp Tyr Phe Glu Tyr Gln Gly Asn Trp Tyr Leu Thr Asp Ala Asn Tyr
        50                  55                  60

Gln Leu Ile Lys Gly Phe Lys Ala Val Asp Asp Ser Leu Gln His Phe
65                  70                  75                  80

Asp Glu Val Thr Gly Val Gln Thr Lys Asp Ser Ala Leu Ile Ser
                85                  90                  95

<210> SEQ ID NO 12
<211> LENGTH: 102
<212> TYPE: PRT
<213> ORGANISM: Artificial Sequence
<220> FEATURE:
<223> OTHER INFORMATION: peptide

<400> SEQUENCE: 12

Ala Lys Thr Gly Phe Val Leu Gln Asp Gly Val Leu Arg Tyr Phe Asp
1               5                   10                  15

Gln Asn Gly Glu Gln Val Lys Asp Ala Ile Ile Val Asp Pro Asp Thr
                20                  25                  30

Asn Leu Ser Tyr Tyr Phe Asn Ala Thr Gln Gly Val Ala Val Lys Asn
            35                  40                  45

Asp Tyr Phe Glu Tyr Gln Gly Asn Trp Tyr Leu Thr Asp Ala Asn Tyr
        50                  55                  60

Gln Leu Ile Lys Gly Phe Lys Ala Val Asp Asp Ser Leu Gln His Phe
65                  70                  75                  80

Asp Glu Val Thr Gly Val Gln Thr Lys Asp Ser Ala Leu Ile Ser Ala
                85                  90                  95

Gln Gly Lys Val Tyr Gln
            100

<210> SEQ ID NO 13
<211> LENGTH: 393
<212> TYPE: DNA
<213> ORGANISM: Leuconostoc mesenteroides

<400> SEQUENCE: 13
aatcagtatt atcaattagc agatggtaaa tatatgttgt tagatgatag tggtcgtgcg      60
aaaacagggt ttgtattgca agatggtgta ctaagatact tcgatcaaaa cggtgagcaa     120
```

```
gtgaaagatg ctatcattgt ggatccagat actaacttga gttattattt caatgcaaca    180
caaggtgtcg ctgtaaaaaa tgattatttc gagtatcaag gtaattggta tttaacagat    240
gctaattatc aacttatcaa aggttttaaa gcagttgacg acagcttaca acattttgat    300
gaagtcactg gtgtacaaac aaaagatagt gctttaataa gtgctcaggg taaggtttac    360
caatttgata ataatggaaa tgctgtgtca gca                                  393

<210> SEQ ID NO 14
<211> LENGTH: 336
<212> TYPE: DNA
<213> ORGANISM: Artificial Sequence
<220> FEATURE:
<223> OTHER INFORMATION: polynucleotide

<400> SEQUENCE: 14
gcgaaaacag ggtttgtatt gcaagatggt gtactaagat acttcgatca aaacggtgag     60
caagtgaaag atgctatcat tgtggaccca gatactaact tgagttatta tttcaatgca    120
acacaaggtg tcgctgtaaa aaatgattat ttcgagtatc aaggtaattg gtatttaaca    180
gatgctaatt atcaacttat caaaggtttt aaagcagttg acgacagctt acaacatttt    240
gatgaagtca ctggtgtaca acaaaagat agtgctttaa taagtgctca gggtaaggtt    300
taccaatttg ataataatgg aaatgctgtg tcagca                              336

<210> SEQ ID NO 15
<211> LENGTH: 330
<212> TYPE: DNA
<213> ORGANISM: Artificial Sequence
<220> FEATURE:
<223> OTHER INFORMATION: polynucleotide

<400> SEQUENCE: 15
aatcagtatt atcaattagc agatggtaaa tatatgttgt tagatgatag tggtcgtgcg     60
aaaacagggt ttgtattgca accagatact aacttgagtt attatttcaa tgcaacacaa    120
ggtgtcgctg taaaaaatga ttatttcgag tatcaaggta attggtattt aacagatgct    180
aattatcaac ttatcaaagg ttttaaagca gttgacgaca gcttacaaca ttttgatgaa    240
gtcactggtg tacaaacaaa agatagtgct ttaataagtg ctcagggtaa ggtttaccaa    300
tttgataata atggaaatgc tgtgtcagca                                     330

<210> SEQ ID NO 16
<211> LENGTH: 345
<212> TYPE: DNA
<213> ORGANISM: Artificial Sequence
<220> FEATURE:
<223> OTHER INFORMATION: polynucleotide

<400> SEQUENCE: 16
aatcagtatt atcaattagc agatggtaaa tatatgttgt tagatgatag tggtcgtgcg     60
aaaacagggt ttgtattgca agatggtgta ctaagatact cgatcaaaa cggtgagcaa    120 gtgaaagatg ctatcattgt ggacccaaaa aatgattatt tcgagtatca aggtaattgg    180
tatttaacag atgctaatta tcaacttatc aaaggtttta aagcagttga cgacagctta    240
caacattttg atgaagtcac tggtgtacaa acaaaagata gtgctttaat aagtgctcag    300
ggtaaggttt accaatttga taataatgga aatgctgtgt cagca                    345

<210> SEQ ID NO 17
<211> LENGTH: 357
```

```
<212> TYPE: DNA
<213> ORGANISM: Artificial Sequence
<220> FEATURE:
<223> OTHER INFORMATION: polynucleotide

<400> SEQUENCE: 17
aatcagtatt atcaattagc agatggtaaa tatatgttgt tagatgatag tggtcgtgcg    60
aaaacagggt ttgtattgca agatggtgta ctaagatact tcgatcaaaa cggtgagcaa   120
gtgaaagatg ctatcattgt ggacccagat actaacttga gttattattt caatgcaaca   180
caaggtgtcg ctgtattaac agatgctaat tatcaactta tcaaaggttt taaagcagtt   240
gacgacagct tacaacattt tgatgaagtc actggtgtac aaacaaaaga tagtgctttt   300
ataagtgctc agggtaaggt ttaccaattt gataataatg gaaatgctgt gtcagca      357

<210> SEQ ID NO 18
<211> LENGTH: 345
<212> TYPE: DNA
<213> ORGANISM: Artificial Sequence
<220> FEATURE:
<223> OTHER INFORMATION: polynucleotide

<400> SEQUENCE: 18
aatcagtatt atcaattagc agatggtaaa tatatgttgt tagatgatag tggtcgtgcg    60
aaaacagggt ttgtattgca agatggtgta ctaagatact tcgatcaaaa cggtgagcaa   120
gtgaaagatg ctatcattgt ggacccagat actaacttga gttattattt caatgcaaca   180
caaggtgtcg ctgtaaaaaa tgattatttc gagtatcaag gtaattggta tttaagctta   240
caacattttg atgaagtcac tggtgtacaa acaaaagata gtgctttaat aagtgctcag   300
ggtaaggttt accaatttga taataatgga aatgctgtgt cagca                   345

<210> SEQ ID NO 19
<211> LENGTH: 342
<212> TYPE: DNA
<213> ORGANISM: Artificial Sequence
<220> FEATURE:
<223> OTHER INFORMATION: polynucleotide

<400> SEQUENCE: 19
aatcagtatt atcaattagc agatggtaaa tatatgttgt tagatgatag tggtcgtgcg    60
aaaacagggt ttgtattgca agatggtgta ctaagatact tcgatcaaaa cggtgagcaa   120
gtgaaagatg ctatcattgt ggacccagat actaacttga gttattattt caatgcaaca   180
caaggtgtcg ctgtaaaaaa tgattatttc gagtatcaag gtaattggta tttaacagat   240
gctaattatc aacttatcaa aggttttaaa gcagttgacg acagcttaca acattttgat   300
gaagtcactg gtgtacaaac aaaagatagt gctttaataa gt                      342

<210> SEQ ID NO 20
<211> LENGTH: 192
<212> TYPE: DNA
<213> ORGANISM: Artificial Sequence
<220> FEATURE:
<223> OTHER INFORMATION: polynucleotide

<400> SEQUENCE: 20
aatcagtatt atcaattagc agatggtaaa tatatgttgt tagatgatag tggtcgtgcg    60
aaaacagggt ttgtattgca aagcttacaa cattttgatg aagtcactgg tgtacaaaca   120
aaagatagtg ctttaataag tgctcagggt aaggtttacc aatttgataa taatggaaat   180
```

```
gctgtgtcag ca                                                        192
```

<210> SEQ ID NO 21
<211> LENGTH: 108
<212> TYPE: DNA
<213> ORGANISM: Artificial Sequence
<220> FEATURE:
<223> OTHER INFORMATION: polynucleotide

<400> SEQUENCE: 21

```
aatcagtatt atcaattagc agatggtaaa tatatgttgt tagatgatag tggtcgtgct    60
cagggtaagg tttaccaatt tgataataat ggaaatgctg tgtcagca               108
```

<210> SEQ ID NO 22
<211> LENGTH: 312
<212> TYPE: DNA
<213> ORGANISM: Artificial Sequence
<220> FEATURE:
<223> OTHER INFORMATION: polynucleotide

<400> SEQUENCE: 22

```
gatggtgtac taagatactt cgatcaaaac ggtgagcaag tgaaagatgc tatcattgtg    60
gacccagata ctaacttgag ttattatttc aatgcaacac aaggtgtcgc tgtaaaaaat   120
gattatttcg agtatcaagg taattggtat ttaacagatg ctaattatca acttatcaaa   180
ggttttaaag cagttgacga cagcttacaa cattttgatg aagtcactgg tgtacaaaca   240
aaagatagtg ctttaataag tgctcagggt aaggtttacc aatttgataa taatggaaat   300
gctgtgtcag ca                                                       312
```

<210> SEQ ID NO 23
<211> LENGTH: 285
<212> TYPE: DNA
<213> ORGANISM: Artificial Sequence
<220> FEATURE:
<223> OTHER INFORMATION: polynucleotide

<400> SEQUENCE: 23

```
gcgaaaacag ggtttgtatt gcaagatggt gtactaagat acttcgatca aaacggtgag    60
caagtgaaag atgctatcat tgtggaccca gatactaact tgagttatta tttcaatgca   120
acacaaggtg tcgctgtaaa aaatgattat ttcgagtatc aaggtaattg gtatttaaca   180
gatgctaatt atcaacttat caaaggtttt aaagcagttg acgacagctt acaacatttt   240
gatgaagtca ctggtgtaca aacaaaagat agtgctttaa taagt                   285
```

<210> SEQ ID NO 24
<211> LENGTH: 309
<212> TYPE: DNA
<213> ORGANISM: Artificial Sequence
<220> FEATURE:
<223> OTHER INFORMATION: polynucleotide

<400> SEQUENCE: 24

```
atggcgaaaa cagggtttgt attgcaagat ggtgtactaa gatacttcga tcaaaacggt    60
gagcaagtga agatgctat cattgtggac ccagatacta acttgagtta tatttcaat   120 gcaacacaag gtgtcgctgt aaaaaatgat tatttcgagt atcaaggtaa ttggtattta   180
acagatgcta attatcaact tatcaaaggt tttaaagcag ttgacgacag cttacaacat   240
tttgatgaag tcactggtgt acaaacaaaa gatagtgctt taataagtgc tcagggtaag   300
gtttaccaa                                                          309
```

<210> SEQ ID NO 25
<211> LENGTH: 45
<212> TYPE: DNA
<213> ORGANISM: Artificial Sequence
<220> FEATURE:
<223> OTHER INFORMATION: primer

<400> SEQUENCE: 25
gatataggta ccaatcagta ttatcaatta gcagatggta aatat            45

<210> SEQ ID NO 26
<211> LENGTH: 42
<212> TYPE: DNA
<213> ORGANISM: Artificial Sequence
<220> FEATURE:
<223> OTHER INFORMATION: primer

<400> SEQUENCE: 26
ctgcaggtcg acttatgctg acacagcatt tccattatta tc               42

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
gatgctatca ttgtggaccc agatactaac ttgag                       35

<210> SEQ ID NO 28
<211> LENGTH: 35
<212> TYPE: DNA
<213> ORGANISM: Artificial Sequence
<220> FEATURE:
<223> OTHER INFORMATION: primer

<400> SEQUENCE: 28
ctcaagttag tatctgggtc cacaatgata gcatc                       35

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gatatacata tggctagcaa aggagaagaa cttttc                      36

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
ctgcagggta cctttgtaga gctcatccat gccatgtg                    38

<210> SEQ ID NO 31
<211> LENGTH: 34
<212> TYPE: DNA
<213> ORGANISM: Artificial Sequence
<220> FEATURE:

<223> OTHER INFORMATION: primer

<400> SEQUENCE: 31
gatataggta ccgcgaaaac agggtttgta ttgc                              34

<210> SEQ ID NO 32
<211> LENGTH: 55
<212> TYPE: DNA
<213> ORGANISM: Artificial Sequence
<220> FEATURE:
<223> OTHER INFORMATION: primer

<400> SEQUENCE: 32
gcattgaaat aataactcaa gttagtatct ggttgcaata caaaccctgt tttcg        55

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
ccagatacta acttgagtta ttatttcaat gc                                32

<210> SEQ ID NO 34
<211> LENGTH: 54
<212> TYPE: DNA
<213> ORGANISM: Artificial Sequence
<220> FEATURE:
<223> OTHER INFORMATION: primer

<400> SEQUENCE: 34
aattaccttg atactcgaaa taatcatttt ttgggtccac aatgatagca tctt         54

<210> SEQ ID NO 35
<211> LENGTH: 31
<212> TYPE: DNA
<213> ORGANISM: Artificial Sequence
<220> FEATURE:
<223> OTHER INFORMATION: primer

<400> SEQUENCE: 35
aaaaatgatt atttcgagta tcaaggtaat t                                 31

<210> SEQ ID NO 36
<211> LENGTH: 54
<212> TYPE: DNA
<213> ORGANISM: Artificial Sequence
<220> FEATURE:
<223> OTHER INFORMATION: primer

<400> SEQUENCE: 36
cctttgataa gttgataatt agcatctgtt aatacagcga caccttgtgt tgca         54

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
ttaacagatg ctaattatca acttatcaaa gg                                32

```
<210> SEQ ID NO 38
<211> LENGTH: 60
<212> TYPE: DNA
<213> ORGANISM: Artificial Sequence
<220> FEATURE:
<223> OTHER INFORMATION: primer

<400> SEQUENCE: 38
cagtgacttc atcaaaatgt tgtaagctta aataccaatt accttgatac tcgaaataat    60

<210> SEQ ID NO 39
<211> LENGTH: 28
<212> TYPE: DNA
<213> ORGANISM: Artificial Sequence
<220> FEATURE:
<223> OTHER INFORMATION: primer

<400> SEQUENCE: 39
agcttacaac attttgatga agtcactg                                        28

<210> SEQ ID NO 40
<211> LENGTH: 48
<212> TYPE: DNA
<213> ORGANISM: Artificial Sequence
<220> FEATURE:
<223> OTHER INFORMATION: primer

<400> SEQUENCE: 40
ctgcaggtcg acttaactta ttaaagcact atcttttgtt tgtacacc                  48

<210> SEQ ID NO 41
<211> LENGTH: 51
<212> TYPE: DNA
<213> ORGANISM: Artificial Sequence
<220> FEATURE:
<223> OTHER INFORMATION: primer

<400> SEQUENCE: 41
cagtgacttc atcaaaatgt tgtaagcttt gcaatacaaa ccctgttttc g              51

<210> SEQ ID NO 42
<211> LENGTH: 58
<212> TYPE: DNA
<213> ORGANISM: Artificial Sequence
<220> FEATURE:
<223> OTHER INFORMATION: primer

<400> SEQUENCE: 42
caaattggta aaccttaccc tgagcacgac cactatcatc taacaacata tatttacc       58

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
gctcagggta aggtttacca atttg                                           25

<210> SEQ ID NO 44
<211> LENGTH: 42
<212> TYPE: DNA
<213> ORGANISM: Artificial Sequence
<220> FEATURE:
<223> OTHER INFORMATION: primer
```

```
<400> SEQUENCE: 44
gatataggta ccgatggtgt actaagatac ttcgatcaaa ac                42

<210> SEQ ID NO 45
<211> LENGTH: 48
<212> TYPE: DNA
<213> ORGANISM: Artificial Sequence
<220> FEATURE:
<223> OTHER INFORMATION: primer

<400> SEQUENCE: 45
ctgcaggtcg acttaactta ttaaagcact atcttttgtt tgtacacc          48

<210> SEQ ID NO 46
<211> LENGTH: 39
<212> TYPE: DNA
<213> ORGANISM: Artificial Sequence
<220> FEATURE:
<223> OTHER INFORMATION: primer

<400> SEQUENCE: 46
ctgcaggtcg acttattggt aaaccttacc ctgagcact                    39

<210> SEQ ID NO 47
<211> LENGTH: 23
<212> TYPE: DNA
<213> ORGANISM: Artificial Sequence
<220> FEATURE:
<223> OTHER INFORMATION: primer

<400> SEQUENCE: 47
cactataggg gaattgtgag cgg                                     23

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
gctagttatt gctcagcggt gg                                      22
```